United States Patent [19]
Pidwerbetsky et al.

[11] Patent Number: 6,084,530
[45] Date of Patent: Jul. 4, 2000

[54] MODULATED BACKSCATTER SENSOR SYSTEM

[75] Inventors: Alex Pidwerbetsky, Randolph; R. Anthony Shober, Red Bank, both of N.J.

[73] Assignee: Lucent Technologies Inc., Murray Hill, N.J.

[21] Appl. No.: 08/777,771

[22] Filed: Dec. 30, 1996

[51] Int. Cl.$^7$ ............................... H04B 1/40; H04B 1/59
[52] U.S. Cl. ............................... 340/825.54; 340/825.49; 340/572; 342/42; 342/51; 342/114
[58] Field of Search ............................ 340/825.54, 825.49, 340/568, 505, 572, 573; 342/42, 51, 47, 104, 114

[56] References Cited

U.S. PATENT DOCUMENTS

| | | |
|---|---|---|
| 3,720,940 | 3/1973 | Fox et al. . |
| 3,939,052 | 2/1976 | Glasson et al. . |
| 3,997,847 | 12/1976 | Tong . |
| 4,068,232 | 1/1978 | Meyers et al. . |
| 4,584,534 | 4/1986 | Lijphart et al. . |

(List continued on next page.)

FOREIGN PATENT DOCUMENTS

| | | |
|---|---|---|
| 0 313 491 A1 | 4/1989 | European Pat. Off. . |
| 0 346 922 A2 | 12/1989 | European Pat. Off. . |
| 0 670 558 A2 | 2/1995 | European Pat. Off. . |
| 0 724 351 A2 | 7/1996 | European Pat. Off. . |
| 0 732 597 A1 | 9/1996 | European Pat. Off. . |
| 0 750 200 | 12/1996 | European Pat. Off. . |
| S63-52082 | 3/1988 | Japan . |
| 1 098 431 | 11/1982 | United Kingdom . |
| 2 193 359 | 2/1988 | United Kingdom . |
| 2 202 415 | 9/1988 | United Kingdom . |
| WO 89/05549 | 6/1989 | WIPO . |
| WO 94/19781 | 9/1994 | WIPO . |

OTHER PUBLICATIONS

Patent No. 3,944,928, Augenblick et al., issued Mar. 16, 1976, Serial No. 484,766, Filed Jul. 1, 1974.
Patent No. 3,984,835, Kaplan et al., issued Oct. 5, 1976, Serial No. 576,604, Filed May 12, 1975.

(List continued on next page.)

*Primary Examiner*—William A. Cuchlinski, Jr.
*Assistant Examiner*—Yonel Beaulieu
*Attorney, Agent, or Firm*—Christopher N. Malvone; Irena Lager

[57] ABSTRACT

A radio communication system includes an Interrogator for generating and transmitting a radio signal. One or more Tags contained within the radio communication system receive the radio signal. A Backscatter Modulator modulates the reflection of the radio signal using a subcarrier signal, thereby forming a reflected modulated signal. The Interrogator receives and demodulates the reflected modulated signal. Based upon the characteristics of the demodulated signal, the Interrogator can determine the identity of the Tag, and the relative velocity of the Tag with respect to the Interrogator. The Interrogator can also determine if motion exists in the vicinity of the Interrogator, even when no Tag is present, without the need for a separate motion detection system. The characteristics of the demodulated signal, can also be used to determine the characteristics of motion of the Tag, such as the vibrational frequency. Alternate embodiments allow the Interrogator to transmit a first information signal to one or more tags, specifying which Tags should respond using Modulated Backscatter, so that the characteristics of only particular Tags can be determined. Further alternate embodiments allow the Tag to input analog data, and perform analog to digital conversion of that data. This data may be then transmitted to the Interrogator using Modulated Backscatter. Alternately, this data may be used as input to calculations performed in the Tag in order to analyze the frequency characteristics of the analog input. The Tag can also, based upon the results of these calculations, identify an abnormal condition and notify the Interrogator of the existence of such a condition.

16 Claims, 6 Drawing Sheets

U.S. PATENT DOCUMENTS

| | | |
|---|---|---|
| 4,656,463 | 4/1987 | Anders et al. . |
| 4,739,328 | 4/1988 | Koelle et al. . |
| 4,827,395 | 5/1989 | Anders et al. . |
| 4,912,471 | 3/1990 | Tyburski et al. . |
| 4,993,068 | 2/1991 | Piosenka et al. . |
| 5,039,994 | 8/1991 | Wash et al. . |
| 5,055,659 | 10/1991 | Hendrick et al. . |
| 5,086,391 | 2/1992 | Chambers . |
| 5,131,038 | 7/1992 | Puhl et al. . |
| 5,164,985 | 11/1992 | Puhl et al. . |
| 5,214,410 | 5/1993 | Verster . |
| 5,227,803 | 7/1993 | O'Connor et al. . |
| 5,251,218 | 10/1993 | Stone et al. . |
| 5,252,979 | 10/1993 | Nysen . |
| 5,264,854 | 11/1993 | Spiess . |
| 5,305,008 | 4/1994 | Turner et al. . |
| 5,317,309 | 5/1994 | Vercellotti et al. . |
| 5,381,137 | 1/1995 | Ghaem et al. . |
| 5,390,339 | 2/1995 | Bruckert et al. . |
| 5,400,949 | 3/1995 | Hirvonen et al. . |
| 5,423,056 | 6/1995 | Linquist et al. . |
| 5,434,572 | 7/1995 | Smith . |
| 5,448,110 | 9/1995 | Tuttle et al. . |
| 5,448,242 | 9/1995 | Sharpe et al. . |
| 5,455,575 | 10/1995 | Schuermann ............................. 342/42 |
| 5,463,402 | 10/1995 | Walrath et al. ........................ 342/359 |
| 5,479,160 | 12/1995 | Koelle . |
| 5,485,520 | 1/1996 | Chaum et al. . |
| 5,491,484 | 2/1996 | Schuermann . |
| 5,510,795 | 4/1996 | Koelle . |
| 5,521,944 | 5/1994 | Hegeler et al. . |
| 5,523,749 | 6/1996 | Cole et al. . |
| 5,525,993 | 6/1996 | Pobanz et al. . |
| 5,525,994 | 6/1996 | Koelle . |
| 5,530,202 | 6/1996 | Dais et al. . |
| 5,543,798 | 8/1996 | Schuermann . |
| 5,559,828 | 9/1996 | Armstrong et al. . |
| 5,572,222 | 11/1996 | Mailandt et al. . |
| 5,581,576 | 12/1996 | Lanzetta et al. . |
| 5,590,158 | 12/1996 | Yamaguchi et al. . |
| 5,600,538 | 2/1997 | Xantopoulous . |
| 5,610,939 | 3/1997 | Takahashi et al. . |
| 5,633,613 | 5/1997 | MacDonald . |
| 5,640,683 | 6/1997 | Evans et al. . |
| 5,649,295 | 7/1997 | Shober et al. ........................ 455/38.2 |
| 5,649,296 | 7/1997 | Maclelian et al. . |
| 5,686,920 | 11/1997 | Hurta et al. . |
| 5,686,928 | 11/1997 | Pritchelt et al. . |
| 5,708,444 | 1/1998 | Pouwels et al. . |

OTHER PUBLICATIONS

Patent No. 4,075,632, Baldwin et al., issued Feb. 21, 1978, Serial No. 689,709, Filed May 24, 1976.

Patent No. 4,360,810, Landt, issued Nov. 23, 1982, Serial No. 226,283, Filed Jan. 19, 1981.

Patent No. 4,471,345, Barrett, Jr., issued Sep. 11, 1984, Serial No. 354,156, Filed Mar. 5, 1982.

Patent No. 4,510,495, Sigrimis et al., issued Apr. 9, 1985, Serial No. 406,471, Filed Aug. 9, 1982.

Patent No. 4,641,374, Oyama, issued Feb. 3, 1987, Serial No. 639,422, Filed Aug. 10, 1984.

Patent No. 4,691,202, Denne et al., issued Sep. 1, 1987, Serial No. 719,551, Filed Apr. 3, 1985.

Patent No. 4,816,839, Landt, issued Mar. 28, 1989, Serial No. 135,048, Filed Dec. 18, 1987.

Patent No. 4,888,591, Landt et al., issued Dec. 19, 1989, Serial No. 254,254, Filed Oct. 6, 1988.

Patent No. 4,937,581, Baldwin et al., issued Jun. 26, 1990, Serial No. 383,169, Filed Jul. 20, 1989.

Patent No. 4,963,887, Kawashima et al., issued Oct. 16, 1990, Serial No. 399,869, Filed Aug. 29, 1989.

Patent No. 5,030,807, Landt et al., issued Jul. 9, 1991, Serial No. 465,428, Filed Jan. 17, 1990.

Patent No. 5,214,409, Biegel, issued May 25, 1993, Serial No. 801,749, Filed Dec. 3, 1991.

Patent No. 5,305,459, Rydel, issued Apr. 19, 1994, Serial No. 49,632, Filed Apr. 19, 1993.

Patent No. 5,339,073, Dodd et al., issued Aug. 16, 1994, Serial No. 674,655, Filed Mar. 25, 1991.

Patent No. 5,347,263, Carroll et al. issued Sep. 13, 1994, Serial No. 14,458, Filed Feb. 5, 1993.

Patent No. 5,420,757, Eberhardt et al., issued May 30, 1995, Serial No. 158,922, Filed Jun. 11, 1993.

Patent No. 5,426,667, van Zon, issued Jun. 20, 1995, Serial No. 77,521, Filed Jun. 17, 1993.

Patent No. 5,461,385, Armstrong, issued Oct. 24, 1995, Serial No. 236,598, Filed Apr. 29, 1994.

Patent No. 5,477,215, Mandelbaum, issued Dec. 19, 1995, Serial No. 100,394, Filed Aug. 2,1993.

Patent No. 5,479,160, Koelle, issued Dec. 26, 1995, Serial No. 130,630, Filed Oct. 1, 1993.

Patent No. 5,479,416, Snodgrass et al., issued Dec. 26, 1995, Serial No. 130,124, Filed Sep. 30, 1993.

"A Microwave Noncontact Identification Transponder Using Subharmonic Interrogation," Carol W. Pobanz, 8099 IEEE Transactions on Microwave Theory and Techniques, 43 (1995), Jul., No. 7, PT. II, New York, US, pp. 1673–1679.

"A Coded Radar Reflector For Remote Identification Of Personnel And Vehicles," Frank R. Williamson, Lacey F. Moore, Ralph Brooks, Julie Anne Williamson, and Melvin C. McGee, Record of the 1993 IEEE National Radar Conference, Lynnefield, MA,USA, Apr. 20–22, 1993, ISBN 0–7803–0934–0, pp. 186–191.

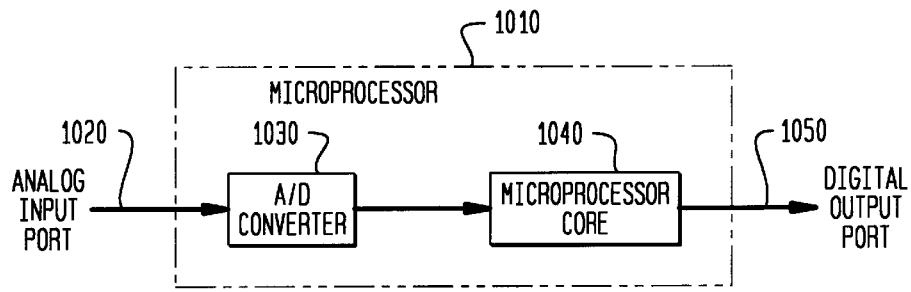
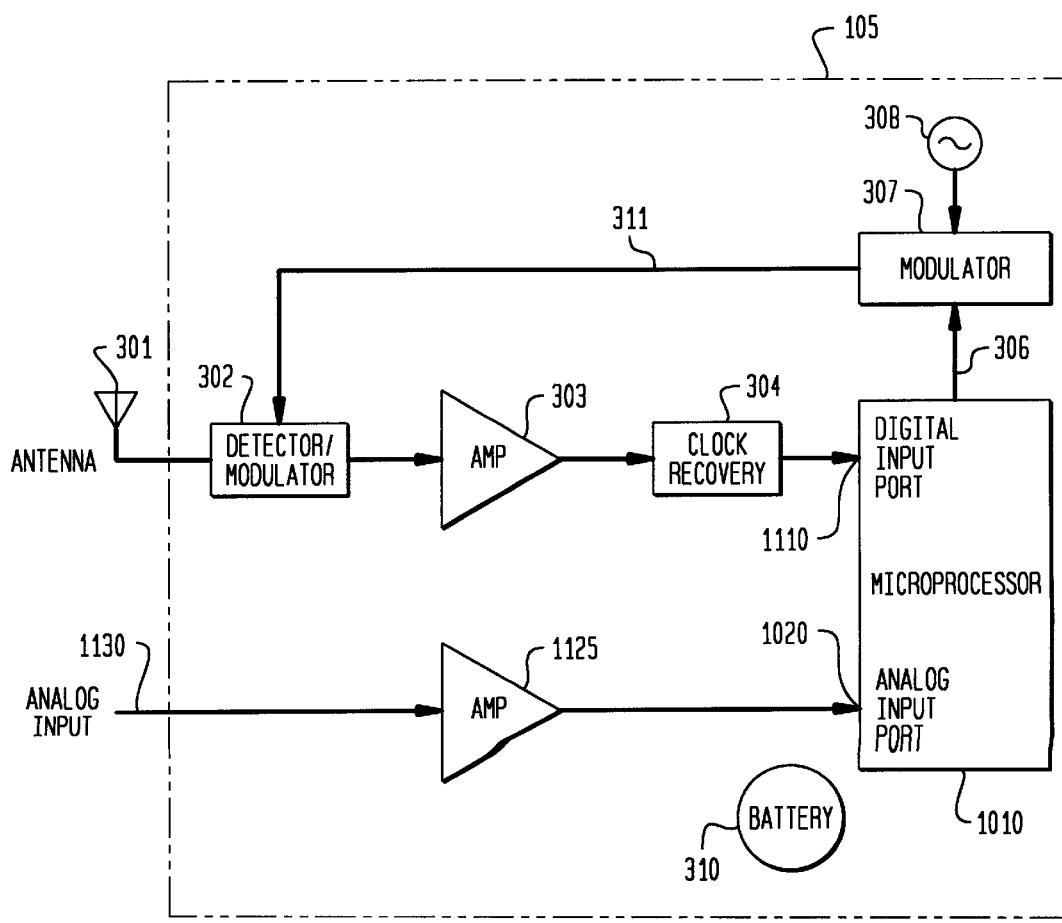

MODULATED BACKSCATTER SENSOR SYSTEM

RELATED APPLICATIONS

Related subject matter is disclosed in the following application filed concurrently herewith and assigned to the same Assignee hereof: U.S. patent applications "Shielding Technology In Modulated Backscatter System", Ser. No. 08/777, 770; "Encryption for Modulated Backscatter Systems", Ser. No. 08/777,812, "Antenna Array In An RFID System", Ser. No. 08/775,217; "Modulated Backscatter Location System", Ser. No. 08/777,643; "QPSK Modulated Backscatter System", Ser. No. 08/775,694; "Subcarrier Frequency Division Multiplexing Of Modulated Backscatter Signals", Ser. No. 08/777,834; "IQ Combiner Technology In Modulated Backscatter System", Ser. No. 08/775,695; "In-Building Personal Pager And Identifier", Ser. No. 08/775,738; "In-Building Modulated Backscatter System", Ser. No. 775,701; "Inexpensive Modulated Backscatter Reflector", Ser. No. 08/774,499; "Passenger, Baggage, And Cargo Reconciliation System", Ser. No. 08/782,026. Related subject matter is also disclosed in the following applications assigned to the same assignee hereof: U.S. patent application Ser. No. 08/504,188, entitled "Modulated Backscatter Communications System Having An Extended Range"; U.S. patent application Ser. No. 08/492,173, entitled "Dual Mode Modulated Backscatter System"; U.S. patent application Ser. No. 08/492,174, entitled "Full Duplex Modulated Backscatter System"; and U.S. patent application Ser. No. 08/571,004, entitled "Enhanced Uplink Modulated Backscatter System."

BACKGROUND OF THE INVENTION

1. Field of the Invention

This invention relates to wireless communication systems and, more particularly, to a wireless communication system using modulated backscatter technology.

2. Description of the Related Art

Radio Frequency Identification (RFID) systems are used for identification and/or tracking of equipment, inventory, or living things. RFID systems are radio communication systems that communicate between a radio transceiver, called an Interrogator, and a number of inexpensive devices called Tags. In RFID systems, the Interrogator communicates to the Tags using modulated radio signals, and the Tags respond with modulated radio signals. After transmitting a message to the Tag (called the Downlink), the Interrogator then transmits a Continuous-Wave (CW) radio signal to the Tag. The Tag then modulates the CW signal using modulated backscattering where the antenna is electrically switched, by the modulating signal, from being an absorber of RF radiation to being a reflector of RF radiation. This modulated backscatter allows communications from the Tag back to the Interrogator (called the Uplink). Conventional Modulated Backscatter (MBS) systems are designed a) to identify an object passing into range of the Interrogator, and b) to store data onto the Tag and then retrieve that data from the Tag at a later time in order to manage inventory or perform some other useful application.

Sensors are used to monitor the current state of a device. An example of a sensor application is to monitor the temperature, pressure, or other characteristic of a mechanical or biological device. Sensor technology has advanced to the point where inexpensive sensors, such as temperature, pressure, etc. can be attached to microprocessors. However, these sensors must communicate their results back to a central control unit.

In another sensor application, we desire to know the relative velocity of a sensor or Tag with respect to a base unit (Interrogator). For example, in an Electronic Toll Collection system, it may be important to not only identify the Tag and store or retrieve data from the Tag, but also determine the velocity of the Tag, perhaps to determine if the vehicle is speeding. In a security access application it would be helpful to identify an object having a Tag, determine the velocity of the Tag, and also to determine if movement is present in the reading field, regardless of whether a Tag is present.

Beyond security, other applications require the ability to monitor sensor outputs. For example, a pump may have a certain vibration "signature" during normal operation, and a different vibration signature during abnormal operation. It is important to ascertain when the pump's vibration signature changes from normal to abnormal.

In some of the described embodiments of this invention, we disclose methods for using MBS RFID systems to perform functions such as, determining the relative velocity of the Tag with respect to the Interrogator, determining if movement is present in the reading field even if not Tag is present, and determining the vibration signature of a device, such as but not limited to a pump, to which the Tag is attached. In this manner, an inexpensive RFID network, consisting of one or more Interrogators, can be constructed which: performs RFID functions, sensor functions, motion detection, and analysis of sensor data functions.

SUMMARY OF THE INVENTION

In accordance with an embodiment of the present invention, a radio communication system includes an Interrogator for generating and transmitting a radio signal. One or more Tags or transponders contained within the radio communication system receive the radio signal. A Backscatter Modulator modulates the reflection of the radio signal using a subcarrier signal, thereby forming a reflected modulated signal. The Interrogator receives and demodulates the reflected modulated signal. Based upon the characteristics of the demodulated signal, the Interrogator can determine the identity of the Tag, and the relative velocity of the Tag with respect to the Interrogator. The Interrogator can also determine if motion exists in the vicinity of the Interrogator, even when no Tag is present, without the need for a separate motion detection system. The characteristics of the demodulated signal, can also be used to determine the characteristics of motion of the Tag, such as the vibrational frequency. Alternate embodiments allow the Interrogator to transmit a first information signal to one or more tags, specifying which Tags should respond using Backscatter Modulator means, so that the characteristics of only particular Tags can be determined. Further alternate embodiments allow the Tag to input analog data, and perform analog to digital conversion of that data. This data may be then transmitted to the Interrogator using Modulated Backscatter. Alternately, this data may be used as input to calculations performed in the Tag in order to analyze the frequency characteristics of the analog input. The Tag can also, based upon the results of these calculations, identify an abnormal condition and notify the Interrogator of the existence of such a condition.

BRIEF DESCRIPTION OF THE DRAWING

FIG. 11 shows how the Tag of FIG. 3 can support analog to digital conversion; and FIG. 12 shows how the Tag of FIG. 3 can support an analog input port.

DETAILED DESCRIPTION

An embodiment of this invention provides a method to integrate motion and velocity determination together with conventional RFID capabilities such as obtaining the identity of an RFID Tag. The RFID Interrogator can determine, based upon the reflected MBS signal from a Tag, certain characteristics of the Tag; such as relative velocity with respect to the Interrogator, and the vibration characteristics of the Tag in the event the Tag is attached to a vibrating object.

MBS Operation

Figure 1:
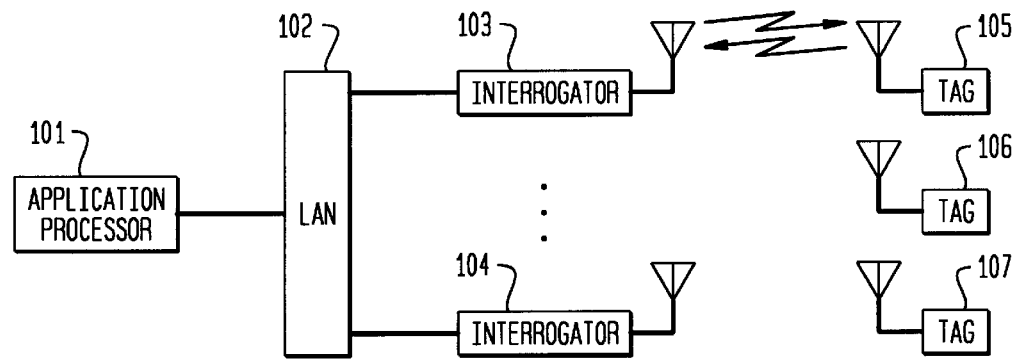
FIG. 1 shows a block diagram of an illustrative Radio Frequency Identification (RFID) system.
Figure 2:
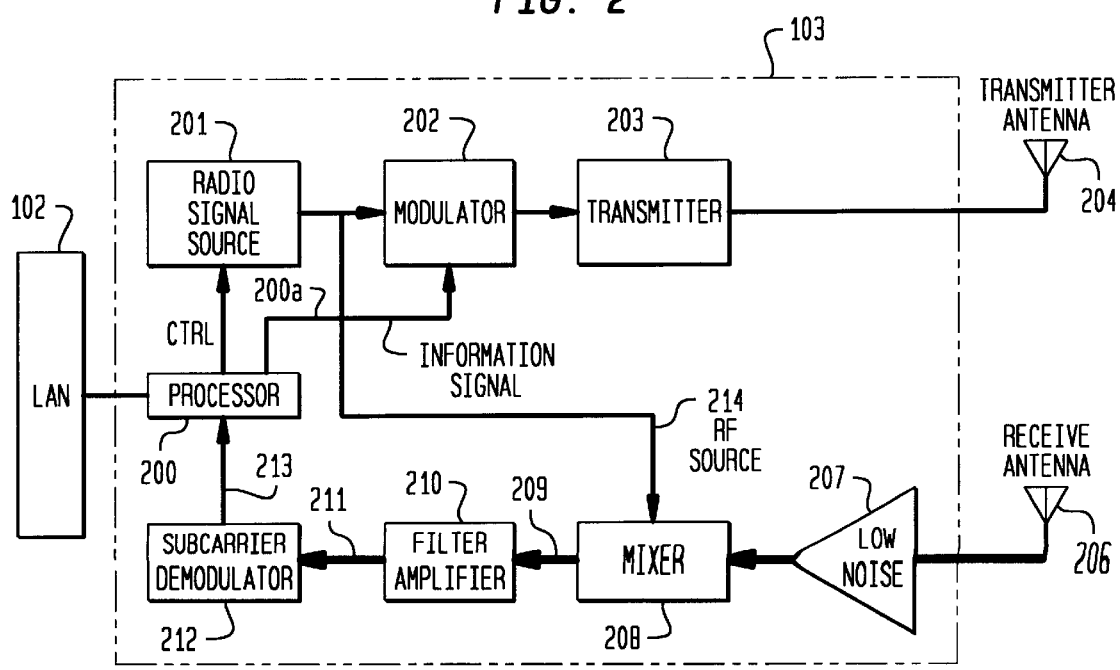
FIG. 2 shows a block diagram of an illustrative Interrogator Unit used in the RFID system of FIG. 1.

We now describe how a RFID system, utilizing MBS, operates. With reference to FIG. 1, there is shown an overall block diagram of a RFID system. An Applications Processor 101 communicates over Local Area Network (LAN) 102 to a plurality of Interrogators 103–104. The Interrogators may then each communicate with one or more of the Tags 105–107. For example and in reference to FIG. 2, the Interrogator 103 receives an information signal, typically from an Applications Processor 101. The Interrogator 103 takes this information signal and Processor 200 formats a Downlink message (Information Signal 200a) to be sent to the Tag. The information signal (200a) may include information such as information specifying which Tag is to respond (each Tag may have fixed or programmed identification number), instructions for the Tag's processor to execute other information to be used and/or stored by the Tag's processor. With joint reference to FIGS. 1 and 2, Radio Signal Source 201 synthesizes a radio signal, the Modulator 202 modulates the radio signal using Information Signal 200a, and the Transmitter 203 transmits this modulated signal via Antenna 204, illustratively using amplitude modulation, to a Tag. Amplitude modulation is a desirable choice because the Tag can demodulate such a signal with a single, inexpensive nonlinear device (such as a diode).

Figure 3:
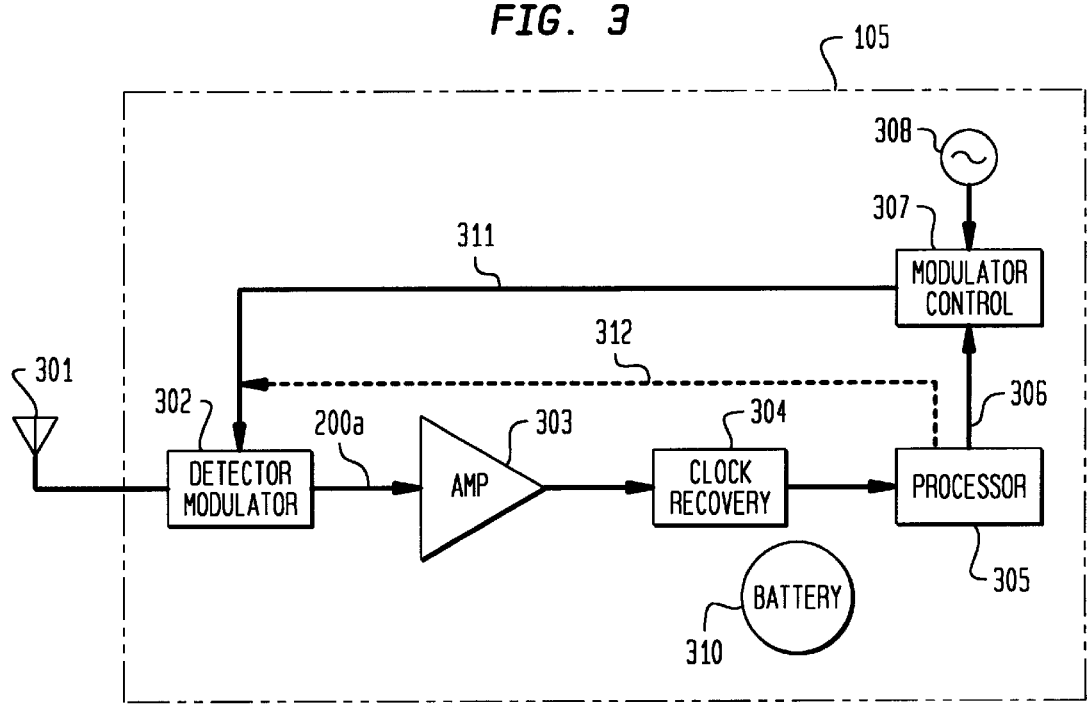
FIG. 3 shows a block diagram of a Tag Unit used in the RFID system of FIG. 1.

In the Tag 105 (see FIG. 3), the Antenna 301 (a loop or patch antenna) receives the modulated signal. This signal is demodulated, directly to baseband, using the Detector/Modulator 302, which, illustratively, could be a single Schottky diode. The result of the diode detector is essentially a demodulation of the incoming signal directly to baseband. The Information Signal 200a is then amplified, by Amplifier 303, and bit synchronization is recovered in Clock Recovery Circuit 304. Clock recovery circuits such as circuits that recover a clock from Manchester encoded data are well known in the art. If large amounts of data are being transferred in frames, frame synchronization may be implemented, for example, by detecting a predetermined bit pattern that indicates the start of a frame. The bit pattern may be detected by clock recovery circuit 304 or processor 305. Bit pattern detection is well known in the art. The resulting information from clock recovery circuit 304 is sent to a Processor 305. The Processor 305 is typically an inexpensive 4 or 8 bit microprocessor and its associated memory, and it generates an Information Signal 306 from the Tag 105 back to the Interrogator (e.g., 103). Information Signal 306 is sent to a Modulator Control Circuit 307, which uses the Information Signal 306 to modulate a subcarrier frequency generated by the Frequency Source 308 to produce signal 311. The Frequency Source 308 may be a crystal oscillator separate from the Processor 305, or a signal derived from the output of a crystal oscillator, or it could be a frequency source derived from signals present inside the Processor 305—such as a divisor of the fundamental clock frequency of the Processor. The Modulated Subcarrier Signal 311 is used by Detector/Modulator 302 to modulate the RF signal received from Tag 105 to produce a modulated backscatter (i.e., reflected) signal. This is accomplished, for example, by switching on and off the Schottky diode of Detector/Modulator 302 using the Modulated Subcarrier Signal 311, thereby changing the reflectance of Antenna 301. A Battery 310 or other power supply provides power to the circuitry of Tag 105. Power may also be received, for example, by using inductive coupling or microwaves.

It has been found that considerable advantages are present to an MBS design that uses a single frequency subcarrier. Many modulation schemes are possible; Phase Shift Keying (PSK) of the subcarrier (e.g., BPSK, QPSK), more complex modulation schemes (e.g., MSK, GMSK), etc.

Returning to FIG. 2, the Interrogator 103 receives the reflected modulated signal with the Receive Antenna 206, amplifies the signal with a Low Noise Amplifier 207, and demodulates the signal using homodyne detection in a Mixer 208. (In an alternative embodiment, a single antenna may replace Transmit antenna (204) and Receive Antenna (206). In this event, an electronic method of canceling the transmitted signal from that received by the receiver chain is needed; this could be accomplished by a device such as a Circulator.)

Using the same Radio Signal Source 201 as used in the transmit chain means the demodulation to baseband is done using Homodyne detection; this has advantages in that it greatly reduces phase noise in the receiver circuits. The Mixer 208 then sends the Demodulated Signal 209 (if Mixer 208 is a Quadrature Mixer, it would send both I (in phase) and Q (quadrature) signals) to the Filter/Amplifier 210. The resulting filtered signal—then typically an Information Signal 211 carried on a subcarrier—is then demodulated from the subcarrier in the Subcarrier Demodulator 212, which then sends the Information Signal 213 to a Processor 200 to determine the content of the message. Subcarrier demolulation may be implemented using a single non-linear device such as diodes or it may be implemented using an analog to digital (A/D) converter and a digital signal processor (DSP) for more complex applications. For example, a diode may be used for amplitude modulated subcarriers and the DSP may be used for PSK modulated subcarriers. The I and Q channels of Signal 209 can be combined in the Filter/Amplifier 210, or in the Subcarrier Demodulator 212, or they could be combined in the Processor 200. Using the above techniques as an example, an inexpensive, short-range, bidirectional digital radio communications channel is implemented. These techniques are inexpensive as the components consist of (for example) a Schottky diode, an amplifier to boost the signal strength, bit and frame synchronization circuits, an inexpensive 4 or 8 bit microprocessor, subcarrier generation circuits, and a battery. Most of these items are already manufactured in large quantities for other applications, and thus are not overly expensive. The circuits mentioned above for bit and frame synchronization and for subcarrier generation may also be implemented in custom logic surrounding the microprocessor core; thus, except for a relatively small amount of chip real estate, these functions come almost "for free."

Relative Velocity

Figure 4:
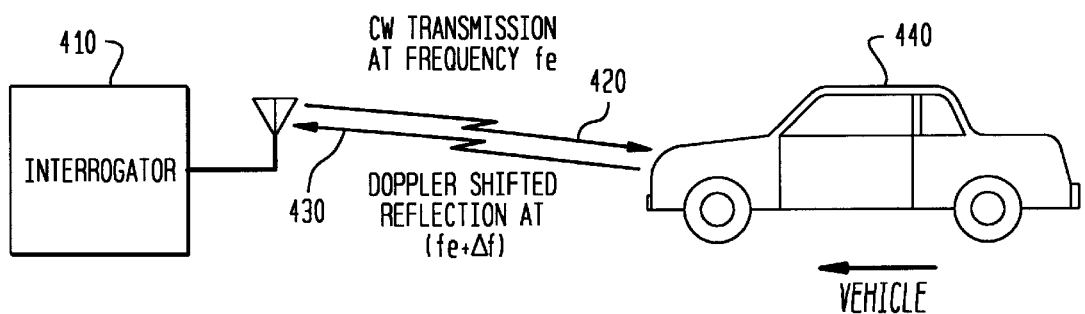
FIG. 4 shows a simplified block diagram of a radar system.

We first discuss how a MBS system is used to determine the relative velocity between an Interrogator and, for example, a vehicle. For this example, assume that the vehicle is moving in a constant direction and at a constant velocity during the period of time the measurement will be taken. To determine the velocity, an MBS similar to a CW police Doppler radar system is used. A simple Doppler radar system, illustrated in FIG. 4, uses a CW signal (420) transmitted from the Interrogator (410) which is reflected by a moving vehicle (440). The reflected signal (430) is frequency shifted ($\Delta_f$, see 430) from the RF carrier ($f_c$, see 420) as a result of a Doppler shift from the moving vehicle. The formula that relates a Radar Doppler Shift ($\Delta_f$) to Relative Velocity (v) is Eq. 1 below. This formula is:

$$v = \Delta_f * \lambda / 2 \qquad (1)$$

where $\lambda$ is the wavelength of the RF carrier $f_c$. The reason Eq. 1 has the factor of "2" is that this is equation is for Radar Doppler Shifts, which have two Doppler Shifts.

Figure 5:
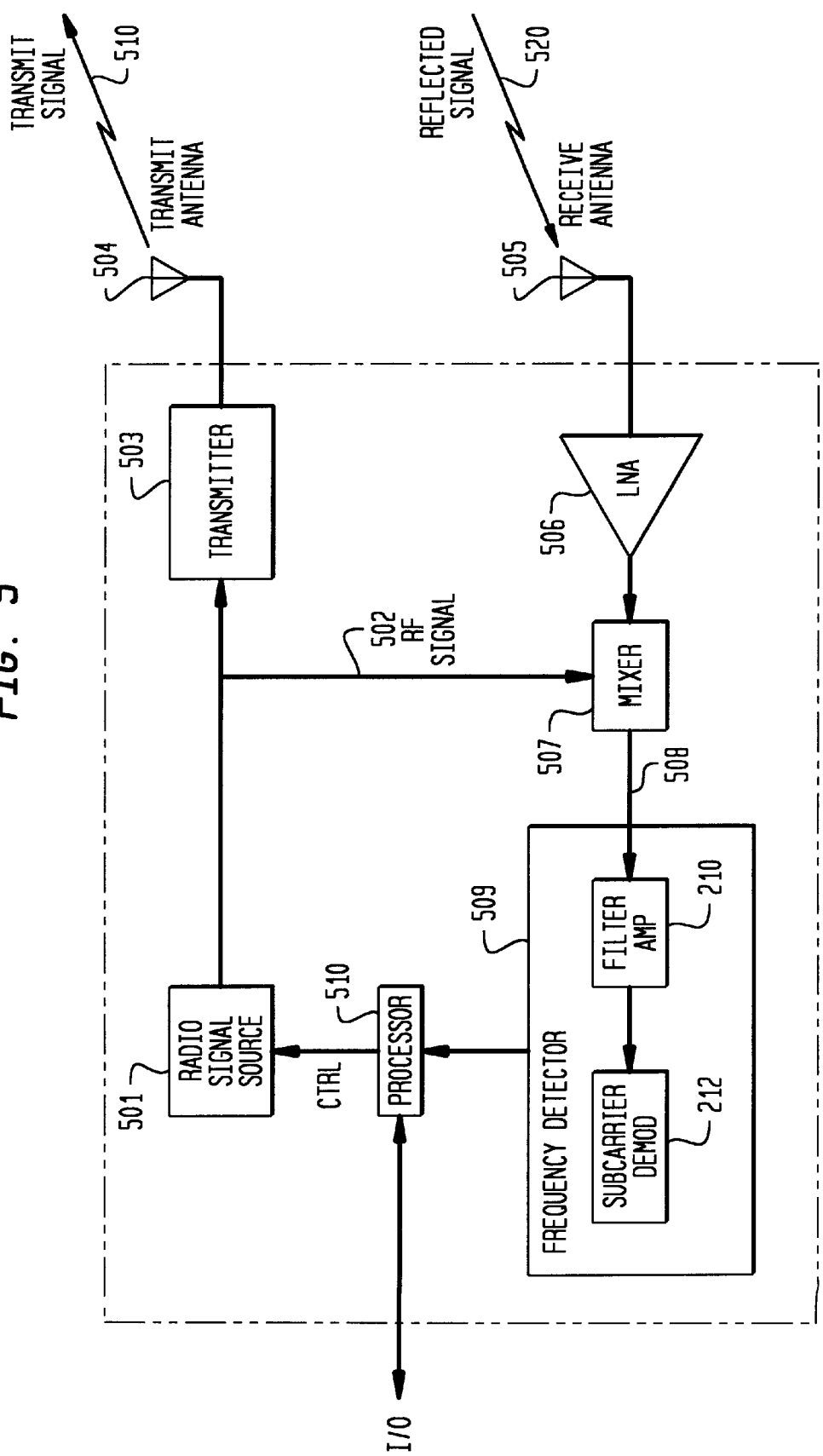
FIG. 5 shows a more detailed block diagram of a RFID Interrogator of a radar system.

The frequency shift $\Delta_f$ is detected in the Interrogator (410) as follows. A more detailed block diagram of an Interrogator implementing this method is shown in FIG. 5. The Radio Signal Source (501) generates a CW RF signal, which is then transmitted by the Transmitter (503) using the Transmit Antenna (504). This signal is called the Transmit Signal (510). The Reflected Signal (520) is received by the Receive Antenna (505) and amplified by the Low Noise Amplifier (506). (Note that radar systems can also be implemented using a single Transmit/Receive Antenna.) The Mixer (507) then mixes the RF Source (502) signal, which comes from the Radio Signal Source (501) to produce signal 508. (The use of the same Radio Signal Source (501) as the input to the Mixer (507) constitutes Homodyne Detection.) The difference between $f_c$ and the frequency of the Reflected Signal (520)—i.e., the Doppler shift—is $\Delta_f$. The frequency of signal 508 is determined by frequency Detector 509, and control processor determines the relative velocity using the frequency. $\Delta_f$ can then be mathematically converted into the relative velocity between the Interrogator and the vehicle, using Eq. 1, since the RF carrier frequency $f_c$ is known. At this point we note the presence of an ambiguity. The above procedure can determine the absolute magnitude of the Doppler shift $\Delta_f$, however in the absence of other information it cannot determine the sign of $\Delta_f$; i.e., it cannot determine whether the Interrogator and the vehicle are moving towards each other or moving away from each other. Other data is required to resolve this ambiguity.

One of the classic difficulties of this approach to velocity determination is that the Doppler shift $\Delta_{71}$ can be relatively small. For example, consider an RF carrier at 2.45 GHz, and a velocity of 10 meters/second. The Doppler shift $\Delta_f$ is then 163 Hz. If one examines the noise spectrum of the output (508) of the Mixer (507), it is common for phase noise to be substantial at this baseband frequency, especially if inadequate isolation exists between the Transmit Antenna (504) and the Receive Antenna (505). Also, since almost everything reflects microwave radiation to some degree, a large amount of reflections are received in a radar system; this is called "clutter." Furthermore, almost any mechanical or electronic device in the radar's field of view not only reflects microwave radiation but also modulates that reflection; e.g., a motor turning at a certain rate will cause modulated reflections at a frequency $\Delta_f$ away from the RF carrier. These modulated reflections will be difficult to distinguish from the Doppler shifted signatures of objects whose velocity is being measured.

Doppler Shifted Subcarrier

Figure 6:
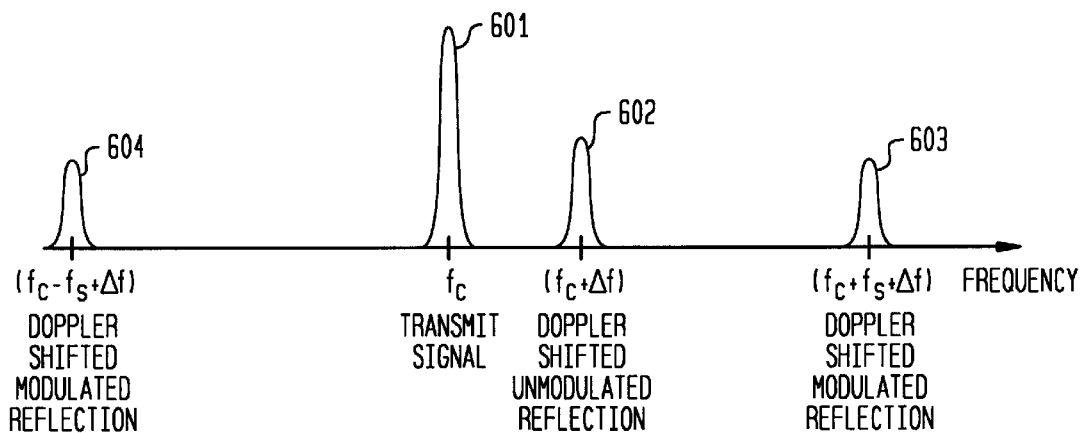
FIG. 6 shows the relative positions of the signals in frequency space before demodulation.
Figure 7:
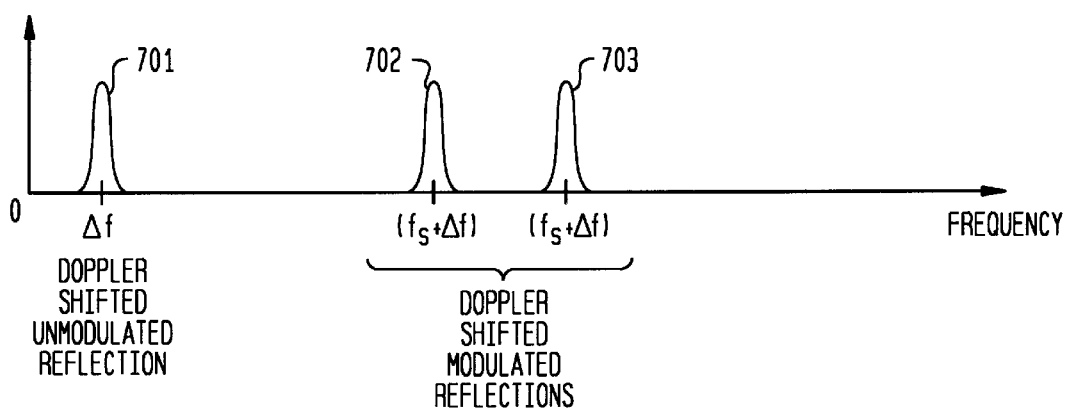
FIG. 7 shows the relative positions of the signals in frequency space after demodulation.

We now disclose a method by which an Interrogator determines the relative velocity between itself and a cooperative Tag by using a Doppler shifted subcarrier. We note that an RFID system can achieve extended range by using a precise frequency subcarrier ($f_s$) digital signal processing, and precise location of the subcarrier with respect to harmonics of the AC power line frequency. In an embodiment of the invention, a narrowband subcarrier at frequency $f_s$ is used. This narrowband subcarrier may be detected at great distances due to the small noise bandwidth, and the fact that the subcarrier is located at a frequency $f_s$ away from the RF carrier frequency $f_c$ such that the "clutter" noise is greatly reduced. We now consider the effects of Doppler on an RFID system using a narrowband subcarrier signal. Assume for simplicity that the RFID Tag is moving towards the Interrogator (a similar analysis holds for the RFID Tag moving away from the Interrogator). Let us use $\Delta_f$ as two-way Doppler shift (as used in Eq. 1). The Interrogator (103) transmits the RF signal at frequency $f_c$ to the Tag (105). The Tag (105) generates the subcarrier frequency $f_s$ within frequency source 308 (see FIG. 3). In one embodiment, assume that the Modulator Control (307) performs no additional modulation. Thus, the frequency $f_c$ is applied to the Detector/Modulator (302), which mixes with the incoming CW frequency at $f_c$. The result of this process are received by the Interrogator 103: a Doppler Shifted Unmodulated Reflection (602), at frequency ($f_c + \Delta_f$), and Doppler Shifted Modulated Reflection (604) at frequency ($f_c - f_s + \Delta_f$) and Doppler Shifted Modulated Reflection (603) at frequency ($f_c + f_s + \Delta_f$). (It should be noted that a more complex derivation of the received signals yield the same results.) The relative positions of these signals are shown in FIG. 6. After demodulation through the Mixer (507), the signals (508) appear as shown in FIG. 7. The Doppler Shifted Unmodulated Reflection (602) is the signal discussed above that is processed in a typical radar system; it generally is of the order of a few hundred Hertz and is thus detectable as a low frequency audible sound. The Doppler Shifted Unmodulated Reflection (602) can be used to determine the relative velocity of an object or objects in the RF field; however, multiple items might be moving in the RF field with different velocities. In this case, multiple Doppler Shifted Unmodulated Reflections (602) with different values of $\Delta_f$ would be present, and it may not be clear which reflection represents the movement of the Tag. This is a classic problem in radar to determine which signal represents the true target, and which signals are "clutter" from other sources of reflection.

Therefore, to measure the relative velocity between the Tag and the Interrogator, we use the Doppler shifted subcarrier signals; thus we are interested in signals 702 and 703, which are the Doppler Shifted Modulated Reflections at baseband frequencies ($f_s - \Delta_f$) and ($f_s + \Delta_f$) respectively. The "bandwidth" of these two signals, or the distance between the center frequency of these signals, is equal to $2\Delta_f$. It should be noted that if the relative velocity between the Interrogator and the Tag is constant, the signals received will be two tones at frequencies $(f_s-\Delta_f)$ and $(f_s+\Delta_f)$, with no signal between these two tones. Thus, we will refer to the "bandwidth" of these signals as the distance between the centers of these tones. As above, we note a fundamental ambiguity in the determination of the sign of $\Delta_f$. Since two identical signals, one located at $(f_s-\Delta_f)$ and another located at $(f_s+\Delta_f)$ are present, it is not possible without additional information to determine whether the Interrogator and the Tag are moving towards each other or moving away from each other. Therefore, to determine the relative velocity between the Tag and an RFID Interrogator similar to the Interrogator of FIG. 2., we filter and amplify the signal 209 through the Filter Amplifier 210. The filter is centered around the subcarrier frequency $f_s$, and would have a bandwidth sufficiently wide to pass the largest $2\Delta_f$ bandwidth signal that is expected. (In practice, if relative velocity is being measured in the same system with traditional RFID communications, the bandwidth of the Filter Amplifier (210) will be wide enough to pass the Uplink signals from Tag to Interrogator, these signals can easily be 100 kHz or more in bandwidth, centered around the subcarrier frequency $f_s$.) To detect the bandwidth $(2\Delta_f)$ of the signal, the Subcarrier Demodulator (212), which for normal RFID communications is used to extract the Information Signal (213) from the demodulated and filtered signal (211), is for this case used to measure the "bandwidth" of the signal present at the subcarrier frequency $f_s$. Once the signal bandwidth $2\Delta_f$ is known, Eq. 1 can be used to calculate the relative velocity v.

To measure the bandwidth of the signal present at the subcarrier frequency $f_s$, several techniques may be used. We note that the frequency $f_s$ is generally much larger than the signal bandwidth $2\Delta_f$. For example, the subcarrier frequency $f_s$ could range from 32 kHz to 1 MHz; while the signal bandwidth $2\Delta_f$ would be 327 Hz (for a velocity of 10 meters/second and an RF carrier frequency of 2.45 GHz). Given the fact that $2\Delta_f$ is much smaller than $f_s$, the Subcarrier Demodulator (212) undersamples the signal, for example at a sample rate of 1–10 kHz, and then processor 510 or a (DSP) within subcarrier demodulator (212) perform a Fourier analysis of the undersampled signal to determine the frequency modes present. The result of this Fourier transform is a direct measurement of $\Delta_f$, since the signals located at $(f_s-\Delta_f)$ and at $(f_s+\Delta_f)$ represent the results of a signal of frequency $\Delta_f$ mixed with a signal of frequency $f_s$.

It should be noted that while we are directly measuring the value of $\Delta_f$, this value is not dependent on the frequency $f_s$. The RFID Tag (103) generates the frequency $f_s$, by using an inexpensive crystal. For example, it is common for inexpensive crystals t have frequency accuracy of (÷100 ppm); therefore a 32 KHz crystal would have a frequency accuracy of ±3.2 Hz. In the above measurement, we are not concerned with exactly where in the frequency domain the signals lie, but rather, once the signals have been located, to accurately determine the value of $\Delta_f$.

Therefore, an MBS RFID system may operate in several different modes. The first mode, called the Interrogation Mode, is where the Tag responds to an request from the Interrogator and transmits, using MBS, data back to the Interrogator. In a second mode, called the Velocity Mode, the Interrogator requests the Tag to respond, not with data, but with a subcarrier tone. Then, using the technique described above, the RFID system determines the relative velocity between the Tag and the Interrogator. Thus, using these two modes, the RFID Tag is identified, and the relative velocity between the Tag and the Interrogator is determined.

Motion Detection

Let us consider a security application in which a person moves in single file through an entrance gate. An RFID Tag, operating in the Interrogation Mode, and located on their person, is the mechanism to authorize entrance to the gate. Furthermore, we must assume that a person cannot pass through the gate without having the proper authorization. One method to accomplish this is to determine if motion is present in the immediate vicinity of the gate; if motion is detected, and no valid Tag is read, then an alarm could be sounded.

Figure 8:
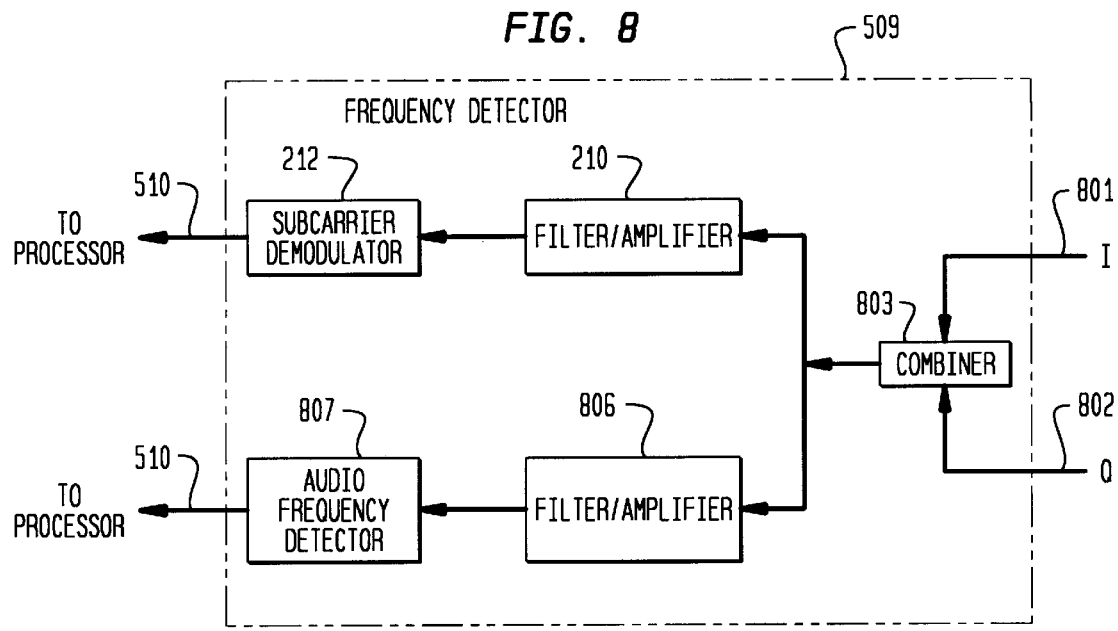
FIG. 8 shows in more detail the Frequency Selector shown in FIG. 7.

The determination of whether motion is present can be accomplished by a relatively minor addition to the Interrogator hardware. FIG. 8 expands the function of the Frequency Detector (509). In one implementation, the output of the Mixer (507) has both I (in-phase) and Q (quadrature) channels. These signals are then be combined in combiner 803 using any one of a number of conventional techniques, for example a simple Summer may be used. The resulting signal is then passed through two different filters; Filter/Amplifier 210 and Filter/Amplifier (806). Filter/Amplifier (806) is a low-pass filter whose passband is no greater than the largest expected Doppler shift. The output of Filter/Amplifier (806) is then processed by an Audio Frequency Detector (807), which determines the Doppler frequency of a moving object in the RF field. Inexpensive implementations of 807 are available due to the widespread use of police and sport radar systems, door openers, etc. Thus, the Interrogator can determine, based on the output of the Audio Frequency Detector (807), if movement exists in the RF field. The signal is also passed through Filter/Amplifier 210, whose filter characteristics are designed to pass a signal centered at the expected subcarrier frequency $f_s$, and with a bandwidth large enough to pass the modulated signal containing the identification data (e.g., a bandwidth of 100 KHz for a 50 kbps BPSK signal).

This capability allows the Interrogator to add another mode of operation. The Interrogator can regularly transmit interrogation messages, addressed to all Tags in the RF field, requesting those Tags to respond with their identification number. Simultaneously, the Interrogator detects if movement exists in the RF field. The sensitivity of the Interrogator to such movement tuned such that the Interrogator only detects movement in the near proximity of the entrance gate. If movement is detected, and no valid Tag is detected, an alarm is sounded.

In addition, the velocity of the Tag with respect to the Interrogator may be determined by the Subcarrier Demodulator (212). Since the Doppler shifted, reflected signal would be centered at the Subcarrier frequency, that signal will be far away from the "clutter" effects discussed above; however the RFID Tag would have a smaller radar cross section than the object to which it was attached. It should be possible to determine the relative velocity of the Tag, using for example the undersampling technique outlined above, at least at the same range or greater than that possible using the conventional Doppler shift technique (i.e., using the output of the Audio Frequency Detector (807)).

Therefore, this technique allows the Interrogator, with very little additional hardware, to function as a motion detector as well as an RFID Interrogator. This obviates the need for a separate motion detection system.

Complex Relative Motion—Vibrational Analysis

In the section above, we have disclosed how to measure the relative velocity of an RFID Tag with respect to an Interrogator. Let us assume an RFID Tag in motion with respect to the Interrogator, and the direction of that motion is along a direct (i.e., line of sight) path from the Interrogator to the Tag. We further assume, as a convenience to illustrate the method, that the primary RF propagation path from Interrogator to the Tag is the direct path, and that the amplitude of the motion varies with time as sin $2\pi\omega t$. Then, the velocity (and hence the Doppler Frequency Shift $\Delta_f$) is proportional to cos $2\pi\omega t$. At time t=0, the velocity is at a maximum, and the Doppler Shifted Modulated Reflections (702, 703) are at their maximum distance apart. At time t=$\pi/2$, the Doppler Frequency Shift $\Delta_f$ is at a minimum, since the velocity is zero. In this case, the two Doppler Shifted Modulated Signals (702, 703) converge to a single signal, not Doppler shifted, and centered at frequency $f_s$. Therefore, the Subcarrier Demodulator (212) must first detect the maximum bandwidth of the signal ($2\Delta_f$), which occurs when the velocity is at a maximum. From the measurement $2\Delta_f$, the maximum velocity of the Tag can be determined. However, there is additional information contained within this signal, as these signals (702, 703) are constantly in motion, moving from being separated at a maximum distance (for t=0 and t=p), and being merged into a single signal (for t=p/2 and t=2p). Therefore, the time variability of this signal will give a measurement of the frequency $\omega$ at which the RFID Tag is vibrating. Thus, the Subcarrier Demodulator (212) also measures the frequency w. In summary, we can obtain two measures using this technique; $\Delta_f$ from which the maximum velocity v can be calculated, and the vibration frequency w. From these two parameters, we can determine a description of the RFID Tag's movement. The only remaining parameter of interest, the amplitude of the vibration—can be calculated given the above two parameters and given the assumption that the vibration is sinusoidal.

Figure 9:
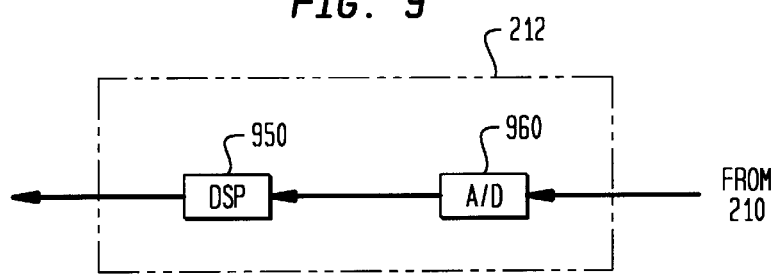
FIG. 9 is a block diagram of a subcarrier demodulator.

The Subcarrier Demodulator (212) performs the functions of determining both $\Delta_f$ and the vibration frequency w. This is a somewhat harder problem than the "Simple Relative Motion" problem above, since the signal is both frequency varying and time varying. One method to determine these parameters is now disclosed. FIG. 9 shows the use of DSP (950) and A/D (960) to perform the function of the Subcarrier Demodulator (212). The output of the Filter Amplifier (210) enters the Subcarrier Demodulator (212) and is sampled at a sampling rate of $2f_s$. For example, if $f_s$ is 32 kHz, then $2f_s$ is 64 kHz. A/D converters that operate at this sampling rate are readily available because of the popularity of audio CD devices. For example, a set of K samples are taken and stored in the storage of a DSP. The number K should be sufficiently large 100 K, since larger values of K increase the signal to noise ratio of the received signal and thus improve the accuracy of the measurements. After the samples are taken, the DSP processes the data. (Note that processing could be done at least partially in real time, given a powerful enough DSP). Conceptually, we wish to divide the frequency space near the subcarrier frequency $f_s$ into a set of frequency bins, and calculate the signal strength in each bin. The signal we expect to see in each bin is the time-averaged signal strength; since the signals have a time-varying value of $\Delta_f$. To calculate the signal strength in each bin, a one-dimensional Fixed Fourier Transform (FFT) can be used. DSP algorithms for FFT's are readily available. Once the signal strength in each bin is found, we can determine $\Delta_f$. The bin containing the frequency $D_f$ is the last bin with significant signal strength; the next bin will have much less signal. Let us call the last bin with significant signal strength as bin j. We therefore have an estimate of $\Delta_f$ to an accuracy of the bandwidth (in Hz) of the bin. This accuracy in $\Delta_f$ corresponds to a certain error in the velocity v, based upon the above equation relating those two parameters. Now that the bin number j is known, we determine the frequency $\omega$ at which signals appear in bin number j. The set of K samples above can then be re-analyzed, now that we know the maximum value of $\Delta_f$. We now wish to determine the time variation of the frequency components within each of the above bins. This determination can be performed by a Two Dimensional Finite Fourier Transform (2D-FFT). This type of computation is common in the analysis of vibrations, and 2D-FFT algorithms such as required here are readily available. Thus, the results of these computations are the value of $\Delta_f$, from which the velocity v can be calculated, and the frequency of oscillation $\omega$.

It was assumed above that the oscillation mode was sinusoidal. However, other vibrational modes are not purely sinusoidal. For example, if the direction of motion is not along the direct path between the Interrogator and the Tag, then a sinusoidal oscillation will not appear as purely sinusoidal when received by the Interrogator. Despite these drawbacks, if the oscillation is periodic and has sufficient mathematical smoothness (e.g., continuous first derivative), then the methods discussed above are still mathematically valid, and FFT algorithms are valid examples of techniques to determine the parameters of interest.

Figure 10:
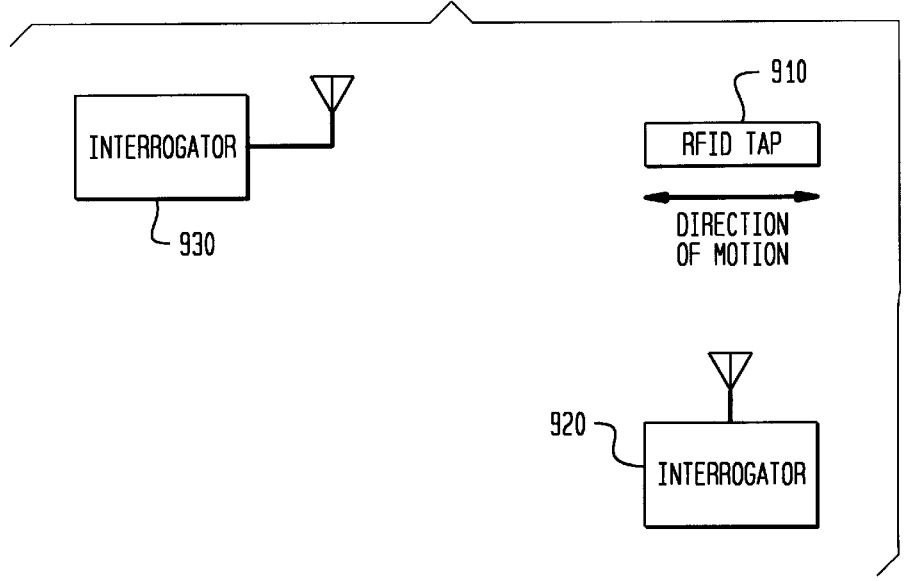
FIG. 10 shows the relative position of multiple Interrogators with respect to an RFID Tag.

We note that the RFID Tag could be moving in a direction other than the direct path between the Tag and the Interrogator. We further note that the primary path of RF propagation may not be along the direct path. These problems can be (at least partially) addressed by placing multiple Interrogators in RF range of the Tag, as shown in FIG. 10. The RFID Tag (910) is vibrating in one direction (as indicated); this direction of vibration would likely not be detected by Interrogator 1 (920). However, Interrogator 2 (930) would be positioned to detect this vibration mode. Note that if the Tag (910) were vibrating in multiple directions simultaneously, then valuable data could be obtained from both Interrogators as to different vibration modes. This concept can be extended to three or more Interrogators within RF range of the Tags. In one embodiment of multiple Interrogators, the system operates with the Interrogators time synchronized. For example, the Interrogators simultaneously transmits the Downlink information, requesting the Tag to respond with its identification number. Each Interrogator, again time synchronized, would transmit a CW tone for the Tag to respond with its identification number using MBS. The Interrogators then transmit a Downlink message, again time synchronized, requesting the Tag to respond with a single subcarrier tone at frequency $f_s$. Each Interrogator transmits on a different RF carrier frequency $f_c$, as this will allow the signals to be received and decoded by each Interrogator independently of each other Interrogator. In this manner, each Interrogator will provide an independent assessment of the relative vibration of the RFID Tag, depending on the orientation of the RFID Tag with respect to that Interrogator. The overall radio communications system can assimilate the input data from each Interrogator to develop an overall assessment of the vibrational modes of the Tag.

Tag Calculations

In the above discussion, we took advantage of the characteristics of the modulated backscattered signal to infer the characteristics of motion of a device to which a Tag (105) was attached. In this discussion, we disclose how to take advantage of the capabilities of the RFID Tag to determine characteristics of motion, such as vibrational analysis, of a device. First, we note today's microprocessors are frequently equipped with A/D converters on board the integrated circuit. Therefore, the Tag architecture discussed may be altered by using microprocessor (1010) in Tag (105). FIG. 11 shows a Microprocessor architecture which allows sensor inputs to be directly sampled. An analog Input Port (1020) is then sampled by an A/D Converter (1030), which is an integral part of the Microprocessor (1010). Typically the Analog Input Port (1020) has an input voltage range from 0 to $V_{cc}$ volts, where $V_{cc}$ is the voltage of the power supply to the Microprocessor Core (1040)—typically three volts. The Analog Input Port (1020) is attached to a Sensor whose output is between 0 to $V_{cc}$ volts. The Tag (105) is first identified by communicating with an interrogator as described above. Then, the Tag is instructed, by information contained within the Information Signal (200a), to begin taking samples of the Sensor input. As discussed above, the sampling rate should be at least two times the maximum frequency present in the sampled signal. The samples are buffered in the Microprocessor Core (1040). In one embodiment, the samples are transmitted to the Interrogator (103), directly as they were sampled, using the modulated backscatter communications link discussed above. Once the signals are received and buffered at the Interrogator (103), the frequency components can be analyzed by using an FFT algorithm as outlined above.

In an alternate embodiment, the Tag (105) could begin to perform all or part of the processing for the FFT algorithm. In an FFT algorithm, the determination of the FFT expansion coefficients $a_k$ and $b_k$ involve arithmetic calculations; where the trigonometric functions required can be pre-calculated and/or pre-stored in a memory device in the Tag (105). Let us assume that a set of samples are taken and stored in the Tag (105). Then, the Tag (105) can begin the necessary calculations. This method could be useful in situations where a Tag must take occasional samples, and then be dormant for a significant part of the time. The fact that the microprocessor on board the Tag (105) is significantly slower at such calculations than a DSP in the Interrogator (103) is not a major drawback. To improve the speed of these calculations, they could be performed in the Tag (105) in fixed-point arithmetic (since most simple 4 or 8 bit microprocessors do not support floating point arithmetic). After the FFT algorithm is completed, the Tag (105) can transmit the values of the parameters $a_k$ and $b_k$ back to the Interrogator (103).

Let us assume that the RFID system wishes to alter the parameters of the FFT algorithm. Such alteration is straight-forward. The values of the trigonometric functions can be pre-calculated by the Interrogator and transmitted to the Tag (105) by placing those values in the Information Signal (200a). In a similar manner, the Tag (105) can be instructed to alter the number of samples taken and the rate at which those samples are taken. Thus, the Tag (105) can be instructed, based on information from the Interrogator (103), to fundamentally alter the type of analysis performed.

An Additional Embodiment

To illustrate the capabilities of another embodiment of this invention, let us describe how to apply these techniques to monitoring of a human heartbeat Conventional techniques involve the connection of wires to the human, and monitoring electronics connected to the wires. The RFID Tag as disclosed here contains much of the electronic necessary to monitor a heartbeat, and has the advantages of being relatively inexpensive and the system being able to monitor a number of such devices at the same time.

Let us enhance the Tag (105) as shown in FIG. 12. The Analog Input (1130) is connected to the patient's chest in a similar manner to that of an electrical lead on an electrocardiogram device. This analog signal is amplified by amplifier (1125) with a maximum signal level of $V_{cc}$, and connected to the Analog Input Port (1020) of the Microprocessor (1010). The A/D Converter (1030) converts this signal to digital format, where it can be analyzed. As above, in one embodiment, the digitized signals are transmitted back to the Interrogator (103), where an FFT algorithm is executed on a DSP to determine the frequency modes of the heartbeat In an alternate embodiment, the Microprocessor (1010) calculates the frequency modes using the FFT algorithm described above. The data can be returned to the Interrogator in one of several ways. The Interrogator (103) could regularly poll all Tags (105) in range of the Interrogator, and request that the Tags transmit back the results of the FFT algorithm calculations (i.e., the values of the parameters $a_k$ and $b_k$). In this manner, the Interrogator could keep track of the heartbeats on a regular basis.

It may become necessary for the Tag (105) to respond very quickly in the event the heartbeat becomes abnormal. Within the FFT algorithm, vibrational modes representing abnormal conditions—such as tachycardia—could be easily identified. These abnormal vibrational modes have recognizable signatures, such as vibration frequencies greater than those normally seen, etc. When the Interrogator polls the Tags (105) for their input data, this Tag (105) could respond with a message indicating that this Tag (105) must immediately transmit its data to the Interrogator. Methods such as using allow multiple Tags to respond simultaneously. Such as using a Slotted Aloha protocol this would allow a Tag (105) to respond almost immediately if an abnormal condition was recognized. Thus, this embodiment of the invention provides an inexpensive device for monitoring vital signals, where a number of such devices can be simultaneously monitored, and the communications to the monitoring devices are performed in a wireless manner.

What has been described is merely illustrative of the application of the principles of the present invention. Other arrangements and methods can be implemented by those skilled in the art without departing from the spirit and scope of the present invention.

The invention claimed is:

1. A modulated backscatter system, comprising:
   at least one transponder that receives a first transmitted signal and modulates a reflected first transmitted signal using a subcarrier signal; and
   at least one interrogator having a transmitter that transmits said first transmitted signal and a receiver that receives said reflected first transmitted signal, said interrogator having a demodulator that obtains a received subcarrier signal from said reflected first transmitted signal, and a subcarrier demodulator that analyzes said received subcarrier signal to measure a motion of said transponder.

2. The modulated backscatter system of claim 1, comprising a first interrogator that transmits said first transmitted signal at a first frequency and a second interrogator that transmits a second transmitted signal at a second frequency, said first and second frequencies being different, and said at least one transponder receiving said second transmitted signal and modulating a reflected second transmitted signal using said subcarrier signal.

3. The modulated backscatter system of claim 1, wherein said demodulator comprises a mixer that mixes said reflected first transmitted signal with another signal to obtain said received subcarrier signal.

4. The modulated backscatter system of claim 1, wherein said demodulator is a homodyne demodulator.

5. The modulated backscatter system of claim 1, wherein said subcarrier demodulator comprises a processor that determines a frequency difference between said received subcarrier signal and said subcarrier signal.

6. A modulated backscatter system, comprising:
   at least one transponder having an antenna that receives a first transmitted signal, a first modulator that modulates a reflected first transmitted signal using a modulated subcarrier signal, a second modulator that modulates a subcarrier signal using an information signal representing information to produce said modulated subcarrier signal, and a processor that receives local information signals and uses said local information signals to produce said information signal; and
   at least one interrogator having a transmitter that transmits said first transmitted signal and a receiver that receives said reflected first transmitted signal, said interrogator having a demodulator that obtains a received modulated subcarrier signal from said reflected first transmitted signal, and a subcarrier demodulator that obtains a received information signal from said received subcarrier signal, said received information signal representing said information.

7. The modulated backscatter system of claim 6, comprising a first interrogator that transmits said first transmitted signal at a first frequency and a second interrogator that transmits a second transmitted signal at a second frequency, said first and second frequencies being different, and said at least one transponder receiving said second transmitted signal and modulating a reflected second transmitted signal using said subcarrier signal.

8. The modulated backscatter system of claim 6, wherein said demodulator comprises a mixer that mixes said reflected first transmitted signal with another signal to obtain said received modulated subcarrier signal.

9. The modulated backscatter system of claim 6, wherein said demodulator is a homodyne demodulator.

10. The modulated backscatter system of claim 6, wherein said subcarrier demodulator comprises a non-linear device.

11. The modulated backscatter system of claim 6, wherein said subcarrier demodulator comprises a processor that determines a frequency difference between said received subcarrier signal and said subcarrier signal.

12. A modulated backscatter system transponder, comprising:
   an antenna that receives a first transmitted signal;
   a first modulator that modulates a reflected first transmitted signal using a modulated subcarrier signal;
   a second modulator that modulates a subcarrier signal using an information signal to produce said modulated subcarrier signal; and
   a processor that receives local information signals and uses said local information signals to produce said information signal.

13. The modulated backscatter system transponder of claim 12, wherein said processor receives local information signals and uses said local information signals to produce said information signal.

14. The modulated backscatter system transponder of claim 12, wherein said processor produces said information signal in response to said first transmitted signal.

15. The modulated backscatter system transponder of claim 12, further comprising a data recovery circuit that obtains data transmitted to the transponder in said first transmitted signal.

16. The modulated backscatter system transponder of claim 15, wherein said processor produces said information signal in response to said data.

* * * * *